(12) United States Patent
Mehrad et al.

(10) Patent No.: US 8,216,796 B2
(45) Date of Patent: Jul. 10, 2012

(54) METHODS FOR TREATING AND DIAGNOSING FIBROTIC AND FIBROPROLIFERATIVE DISEASES

(75) Inventors: Borna Mehrad, Charlottesville, VA (US); Marie D. Burdick, Charlottesville, VA (US); David A. Zisman, Santa Barbara, CA (US); Michael P. Keane, Dublin (IE); John A. Belperio, Los Angeles, CA (US); Robert M. Strieter, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/327,025

(22) Filed: Dec. 15, 2011

(65) Prior Publication Data

US 2012/0094305 A1    Apr. 19, 2012

Related U.S. Application Data

(62) Division of application No. 12/516,912, filed as application No. PCT/US07/86167 on Nov. 30, 2007, now Pat. No. 8,114,608.

(60) Provisional application No. 60/872,019, filed on Nov. 30, 2006.

(51) Int. Cl.
   *G01N 33/53* (2006.01)
(52) U.S. Cl. .......................................... 435/7.1; 435/7.2
(58) Field of Classification Search .................. None
   See application file for complete search history.

(56) References Cited

U.S. PATENT DOCUMENTS

| 7,666,432 B2 | 2/2010 | Gomer et al. |
| 2004/0022774 A1 | 2/2004 | Rice et al. |
| 2005/0215606 A1 | 9/2005 | Torday et al. |
| 2005/0238620 A1 | 10/2005 | Gomer et al. |

OTHER PUBLICATIONS

Philips et al. J. Clinical Investi 2004 vol. 114, p. 438-446.*
Nanki et al., "Chemokines Regulate IL-6 and IL-8 Production by Fibroblast-Like Synoviocytes from Patients with Rheumatoid Arthritis," Journal of Immunology 2001, vol. 167, pp. 5381-5385.
Phillips et al., "Circulating Fibrocytes Traffic to the Lungs in Response to CXCL12 and Mediate Fibrosis," Journal of Clinical Investigation, 2004, vol. 114, No. 3, pp. 438-446.
Quan et al., "Circulating Fibrocytes; collagen-secreting cells of the peripheral blood," Int'l. Journal of Biochemistry & Cell Biology, 36 (2004), pp. 598-606.
Nihlberg et al., "Tissue fibrocytes in patients with mild asthma: A possible link to thickness of reticular basement membrane?", Respiratory Research 2006 LNKD-PUBMED: 16571120, vol. 7, 50, Mar. 2006, pp. 1-9.
Tatiana et al., "Fibrocytes migrate from the bone marrow and blood to the injured liver," XP002583298, Database BIOSI (Online), Biosciences Information Service, Philadelphia, PA, Apr. 2006, pp. 1-2.
Mehrad et al., "Circulating peripheral blood fibrocytes in human fibrotic interstitial lung disease," Biochemical and Biophysical Research Communications, 353 (2007, pp. 104-108.

\* cited by examiner

*Primary Examiner* — Jacob Cheu
(74) *Attorney, Agent, or Firm* — Barnes & Thornburg LLP

(57) ABSTRACT

The present invention provides compositions and methods for diagnosing and treating fibrotic lung disease. In one embodiment the diagnostic method comprises determining the amount of circulating CXCL-12 in a patient relative to a control.

7 Claims, 3 Drawing Sheets

METHODS FOR TREATING AND DIAGNOSING FIBROTIC AND FIBROPROLIFERATIVE DISEASES

RELATED INVENTIONS

This application is a Divisional of U.S. patent application Ser. No. 12/516,912, which is a US national counterpart of international application serial no. PCT/US07/86167, filed Nov. 30, 2007 which claims priority to U.S. Provisional Patent Application No. 60/872,019, filed Nov. 30, 2006, the disclosures of which are herein incorporated by reference in their entirety.

STATEMENT REGARDING FEDERALLY SPONSORED RESEARCH OR DEVELOPMENT

This invention was supported in part from Grant Nos. HL73848, HL080206, AR055075, CA87879, and HL66027 awarded by the National Institutes of Health. The United States Government has certain rights in the invention.

FIELD OF THE INVENTION

This invention relates to methods of treating and diagnosing a subject with a fibrotic or fibroproliferative disease.

BACKGROUND

It has been estimated that up to 45% of deaths in the United States can be attributed to fibroproliferative diseases, which can affect many tissues and organ systems. Fibrosis affects nearly all tissues and organ systems. Diseases in which fibrosis is a major cause of morbidity and mortality include the interstitial lung diseases, liver cirrhosis, liver fibrosis resulting from chronic hepatitis B or C infection, kidney disease, heart disease, and systemic sclerosis. Fibroproliferative disorders also include systemic and local scleroderma, keloids and hypertrophic scars, atherosclerosis, restenosis, and eye diseases including macular degeneration and retinal and vitreal retinopathy. Additional fibrotic disorders include excessive scarring resulting from surgery, chemotherapeutic drug-induced fibrosis, radiation-induced fibrosis, and injuries and burns. Fibrotic tissue remodeling can also influence cancer metastasis and accelerate chronic graft rejection in transplant recipients [28].

Fibrosis is central to the pathogenesis of many chronic lung disorders, including asthma, pneumoconioses, and many infections. The quintessential fibrotic lung diseases, however, are the fibrotic interstitial lung diseases, usual interstitial pneumonia (UIP) and fibrotic variant of non-specific interstitial pneumonia (NSIP). These illnesses are of unknown cause and are characterized by progressive lung fibrosis, typically culminating in respiratory failure and premature death. No treatment has been clearly effective in altering the clinical course of these diseases, and there is an urgent need for better understanding of their pathogenesis [1].

Dysregulated tissue remodeling is fundamental to the development of fibrotic lung diseases: UIP and fibrotic NSIP share the histologic features of relatively mild leukocyte infiltration but prominent accumulation of extracellular matrix in the form of dense or loose fibrosis [2]. They are distinguished by the variegated pattern of pathology in UIP, in which normal areas are juxtaposed with areas with leukocyte infiltration and other areas with advanced fibrosis, whereas fibrotic NSIP is homogenous in its distribution [3-5]. In addition, the pathological lesion of fibroblastic foci, which consist of concentrated numbers of fibroblasts and myofibroblasts associated with focal injury and generation of new collagen, is more prominent in UIP than fibrotic NSIP [6-8].

The source of lung fibroblasts and myofibroblasts is a critical question in the pathogenesis of fibrotic diseases such as lung fibrotic diseases. While these cells were classically thought to be derived exclusively from resident lung fibroblasts, recent studies indicate that they can differentiate from pulmonary epithelial cells [9] and from a circulating precursor cell, the fibrocyte [10]. Fibrocytes are bone marrow-derived cells with monocytic morphology, that express surface markers of leukocytes and haematopoietic stem cells but also collagen-I; and are capable of differentiating into diverse cell types [11-13]. It has been previously shown that, in a mouse model of bleomycin-induced pulmonary fibrosis, both mouse and human fibrocytes can traffic to the lung and contribute to collagen deposition and accumulation of $\alpha$-smooth muscle actin ($\alpha$SMA)-expressing cells in the lung [10]. Furthermore, the recruitment of these cells was mediated via the interaction of the chemokine ligand, CXCL12, in the lung and the receptor, CXCR4, on fibrocytes.

There is a long felt need in the art for methods to diagnose and treat fibrotic disease. The present invention satisfies these needs.

SUMMARY OF THE INVENTION

The present invention encompasses the contribution of fibrocytes to fibrotic and fibroproliferative diseases including, but not limited to, human fibrotic interstitial lung disease. The studies disclosed in the present application compared human lung tissue and peripheral blood from patients with UIP and fibrotic NSIP to normal controls, for the expression of the fibrocyte-attracting chemokine, CXCL12, and presence and number of circulating fibrocytes and their expression of the CXCL12 receptor, CXCR4. Without wishing to be bound by any particular theory, the data disclosed herein indicate that the number of circulating fibrocytes may represent a novel biomarker in patients with fibrotic disorders.

The present application discloses enhanced expression of CXCL12 in both the fibrotic organ and plasma of patients with a fibrotic disease, specifically, the lungs and plasma of patients with lung fibrosis. CXCL12 levels were associated with an order of magnitude higher number of circulating fibrocytes in the peripheral blood of these patients. Most of the circulating fibrocytes in patients with interstitial lung diseases were negative for the myofibroblast marker $\alpha$-smooth muscle actin, suggesting a relatively undifferentiated phenotype. Without wishing to be bound by any particular theory, the data disclosed herein suggest that fibrocytes are involved in the pathogenesis of human fibrosis.

Although the results discussed above relate to experiments performed in a human lung fibrosis model, a skilled artisan would recognize that the results are applicable to a broad range of fibrotic diseases and conditions.

In one embodiment, the present invention encompasses a method of diagnosing a subject with fibrotic disease or disorder. In one aspect, a fibrotic disease or disorder is diagnosed by determining the number of circulating fibrocytes, wherein an increase in the number of circulating fibrocytes in a subject, relative to the number of circulating fibrocytes in a second subject who does not have a fibrotic disease or disorder, is an indication that the first subject has a fibrotic disease or disorder. The first subject is a test subject and the second subject is a control subject. Tissue or peripheral blood samples can be used to determine the number of circulating fibrocytes in the test subject and control subject. Tissue or peripheral blood samples can be obtained by methods known in the art (e.g., venipuncture or biopsy) prior to assaying the number of circulating fibrocytes. Methods known in the art, including, but not limited to, flow cytometry, can be used to determine the number of fibrocytes in the test samples.

In another aspect, a fibrotic disease or disorder is diagnosed by determining the amount of circulating CXCL12, wherein an increase in the amount of circulating CXCL12 in a subject, relative to the amount of circulating CXCL12 in a second subject who does not have fibrotic disease or disorder, is an indication that the first subject has a fibrotic disease or disorder. In one aspect, the subject is a human. The first subject is a test subject and the second subject is a control subject. Tissue or peripheral blood samples can be used to determine CXCL12 levels in the test subject and control subject. Tissue or peripheral blood samples can be obtained by methods known in the art (e.g., venipuncture or biopsy) prior to assaying levels of CXCL12. Methods known in the art for determining protein levels, including, but not limited to, ELISA, immunohistochemical staining and western blot analysis, can be used to determine the number of fibrocytes in the test samples.

In one aspect, the number of circulating fibrocytes in a subject with a fibrotic disease or disorder is at least about 10% greater than in a normal subject. In one aspect, the number of circulating fibrocytes in a subject with a fibrotic disease or disorder is at least about 20% greater than in a normal subject. In one aspect, the number of circulating fibrocytes in a subject with a fibrotic disease or disorder is at least about 30% greater than in a normal subject. In one aspect, the number of circulating fibrocytes in a subject with a fibrotic disease or disorder is at least about 40% greater than in a normal subject. In one aspect, the number of circulating fibrocytes in a subject with a fibrotic disease or disorder is at least about 50% greater than in a normal subject. In one aspect, the number of circulating fibrocytes in a subject with a fibrotic disease or disorder is at least about two times greater than in a normal subject. In one aspect, the number of circulating fibrocytes in a subject with a fibrotic disease or disorder is at least about five times greater than in a normal subject. In another aspect, the number of circulating fibrocytes in a subject with a fibrotic disease or disorder is at least about ten times greater than in a normal subject.

The present invention provides compositions and methods for identifying and quantifying circulating fibrocytes. In one aspect, circulating fibrocytes are selected as collagen-I expressing CD45+ cells. The present invention further encompasses CXCR4+ and CXCR4− subsets of fibrocytes. In another aspect, the circulating fibrocytes also express αSMA. Other techniques are also available and are known to those of ordinary skill in the art.

In one aspect, the amount of circulating CXCL12 in a subject with a fibrotic disease or disorder is at least about 10% greater than in a normal subject. In another aspect, the amount of circulating CXCL12 in a subject with a fibrotic disease or disorder is at least about 20% greater than in a normal subject. In one aspect, the amount of circulating CXCL12 in a subject with a fibrotic disease or disorder is at least about 30% greater than in a normal subject. In yet another aspect, the amount of circulating CXCL12 in a subject with a fibrotic disease or disorder is at least about 50% greater than in a normal subject. In a further aspect, the amount of circulating CXCL12 in a subject with a fibrotic disease or disorder is at least about 100% greater than in a normal subject. In one aspect, the amount of circulating CXCL12 in a subject with a fibrotic disease or disorder is at least about 500% greater than in a normal subject. In another aspect, the amount of circulating CXCL12 in a subject with a fibrotic disease or disorder is at least about 1000% greater than in a normal subject. The present invention further provides methods and composition for detecting and quantifying circulating CXCL12.

In one embodiment, the fibrotic disease or disorder affects the subject's lung(s), liver, kidney(s), heart, eye(s), vasculature, gall bladder or skin. In one embodiment of the invention, the fibrotic disease or disorder affects more than one organ or system. Fibrotic diseases that can be diagnosed and treated by the methods of the invention include, but are not limited to, idiopathic pulmonary fibrosis, fibrotic interstitial lung disease, interstitial pneumonia, fibrotic variant of non-specific interstitial pneumonia, cystic fibrosis, lung fibrosis, silicosis, asbestosis, asthma, chronic obstructive pulmonary lung disease (COPD), pulmonary arterial hypertension, liver fibrosis, liver cirrhosis, renal fibrosis, glomerulosclerosis, x kidney fibrosis, diabetic nephropathy, heart disease, fibrotic valvular heart disease, systemic fibrosis, rheumatoid arthritis, excessive scarring resulting from surgery, chemotherapeutic drug-induced fibrosis, radiation-induced fibrosis, macular degeneration, retinal and vitreal retinopathy, atherosclerosis, and restenosis.

In another embodiment of the invention, the fibrotic or fibroproliferative disease is a lung disease such as fibrotic interstitial lung disease. In one aspect, the fibrotic interstitial lung disease is UIP. In another aspect, it is NSIP.

In one embodiment, at least a subpopulation of the circulating fibrocytes in a subject with fibrocyte lung disease or disorder exhibit a greater degree of differentiation into myofibroblasts than the circulating fibrocytes in a subject who does not have a fibrotic lung disease or disorder.

In one embodiment, the present invention encompasses treating a subject with a fibrotic disease or disorder. In one aspect, the treatment comprises decreasing the number of circulating fibrocytes in the subject. In a further aspect, the treatment comprises decreasing the number of circulating fibrocytes in the subject and reducing plasma CXCL12 levels. In a further aspect, the treatment comprises decreasing the number of circulating fibrocytes in the subject and reducing the total percentage of circulating fibrocytes expressing α-SMA or differentiated into myofibroblasts. In one aspect, the treatment comprises administering to the subject an effective amount of at least one compound, drug, peptide, antibody, aptamer, or other agent, or a combination thereof, capable of inhibiting fibrocyte proliferation or which is toxic to circulating fibrocytes.

The present invention also includes preventing or reducing the effects of a fibrotic disease or disorder in a subject by decreasing the number of circulating fibrocytes in the subject. In a further aspect, the method comprises decreasing the number of circulating fibrocytes in the subject and reducing plasma CXCL12 levels. In a further aspect, the method comprises decreasing the number of circulating fibrocytes in the subject and reducing the total percentage of circulating fibrocytes expressing α-SMA or differentiated into myofibroblasts. In one aspect, the method comprises administering to the subject an effective amount of at least one compound, drug, peptide, antibody, aptamer, or other agent, or a combination thereof, capable of inhibiting fibrocyte proliferation or which is toxic to circulating fibrocytes.

DETAILED DESCRIPTION

Figure 1A:
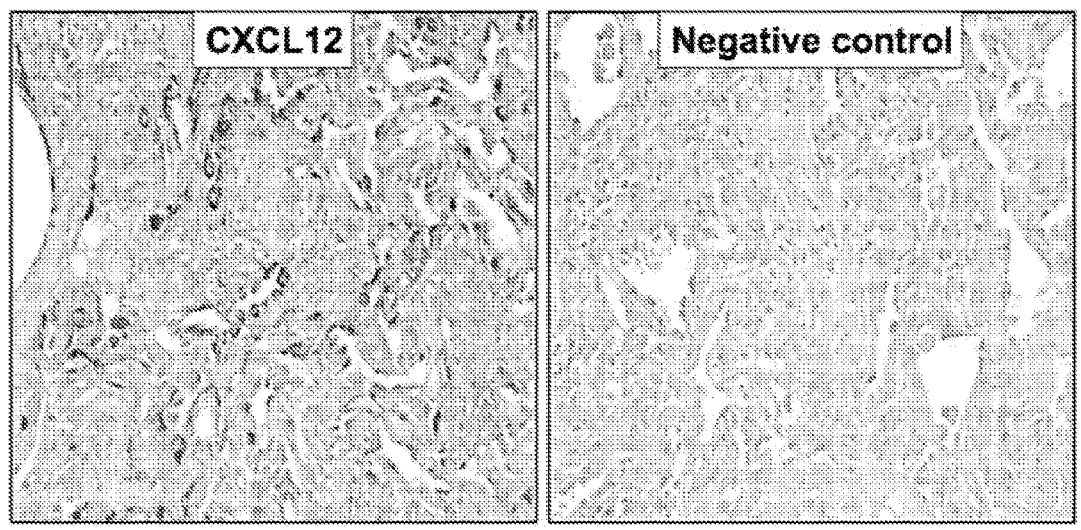
FIG. 1. Lung CXCL12 in fibrotic interstitial lung disease. (a) Immunohistochemical detection of CXCL12 protein in the lung of a patient with UIP. (b) Lung CXCL12 levels measured by ELISA in lung homogenates. Box and whiskers represent 25th-75th and 10th-90th percentiles, respectively; small squares and transverse lines represent the mean and median, respectively. NSIP, lung biopsy from patients with fibrotic non-specific interstitial pneumonia; UIP, lung biopsy from patients with histologic UIP; *, p<0.05 compared to normal lung samples (n=92 for normal lungs, 13 for fibrotic NSIP, 56 for UIP).

Abbreviations and Acronyms
αSMA—α-smooth muscle actin
DAB—3,3'-diaminobenzidine
NSIP—non-specific interstitial pneumonia
UIP—usual interstitial pneumonia Definitions In describing and claiming the invention, the following terminology will be used in accordance with the definitions set forth below.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |

-continued

| Full Name | Three-Letter Code | One-Letter Code |
|---|---|---|
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

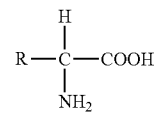

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "biologics," as used herein, refers to biological therapeutics. Biologics include, but are not limited to a peptides, proteins, nucleic acids, antibodies, aptamers, and toxins.

The terms "cell culture" and "culture," as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

The phrases "cell culture medium," "culture medium" (plural "media" in each case) and "medium formulation" refer to a nutritive solution for cultivating cells and may be used interchangeably.

A "control" as used herein may be a positive or negative control as known in the art and can refer to a control cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. For instance, as can be appreciated by a skilled artisan, a control may comprise data (e.g., the number of circulating fibrocytes and/or amount of CXCL12) from one or more control subjects that is stored in a reference database. The control may be a subject who is similar to the test subject (for instance, may be of the same gender, same race, same general age and/or same general health) but who is known to not have a fibrotic disease.

As can be appreciated by a skilled artisan, the methods of the invention can also be modified to compare a test subject to a control subject who is similar to the test subject (for instance, may be of the same gender, same race, same general age and/or same general health) but who is known to have a well characterized fibrotic disease, for instance, a particular stage of a fibrotic disease. In this embodiment, a diagnosis of a fibrotic disease or staging of a fibrotic disease can be made by determining whether the fibrocyte levels or CXCL12 levels are statistically about the same between the test and control subjects.

A "fibrotic" disease or a "fibroproliferative" disease refers to a disease characterized by scar formation and the over production of extracellular matrix by connective tissue. Fibrotic disease occurs as a result of tissue damage. It can occur in virtually every organ of the body. Examples of fibrotic or fibroproliferative diseases include, but are not limited to, idiopathic pulmonary fibrosis, fibrotic interstitial lung disease, interstitial pneumonia, fibrotic variant of non-specific interstitial pneumonia, cystic fibrosis, lung fibrosis, silicosis, asbestosis, asthma, chronic obstructive pulmonary lung disease (COPD), pulmonary arterial hypertension, liver fibrosis, liver cirrhosis, renal fibrosis, glomerulosclerosis, x kidney fibrosis, diabetic nephropathy, heart disease, fibrotic valvular heart disease, systemic fibrosis, rheumatoid arthritis, excessive scarring resulting from surgery, chemotherapeutic drug-induced fibrosis, radiation-induced fibrosis, macular degeneration, retinal and vitreal retinopathy, atherosclerosis, and restenosis. Fibrotic disease or disorder, fibroproliferative disease or disorder and fibrosis are used interchangeably herein.

A "test" cell is a cell being examined. A "test" sample is a sample being examined. In one embodiment, a test sample is obtained from a subject suspected of having a disease or disorder for which the test is being performed. A "test subject" is a subject being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

A "compound", as used herein, refers to any type of substance or agent that is commonly considered a chemical, drug, or a candidate for use as a drug, as well as combinations and mixtures of the above.

The use of the word "detect" and its grammatical variants is meant to refer to measurement of the species without quantification, whereas use of the word "determine" or "measure" with their grammatical variants are meant to refer to measurement of the species with quantification.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

"Disease" and "disorder" are used interchangeably herein. A disease, condition, or disorder is "alleviated" or "treated" if the severity of a symptom of the disease or disorder, the frequency with which such a symptom is experienced by a patient, or both, are reduced.

As used herein, an "effective amount" means an amount of a compound or agent sufficient to produce a selected or desired effect. The term "effective amount" is used interchangeably with "effective concentration" herein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound or any agent to reduce or impede a described function. Preferably, inhibition is by at least 10%, more preferably by at least 25%, even more preferably by at least 50%, and most preferably, the function is inhibited by at least 75%.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein, the term "imaging agent" means a composition of matter which, when delivered to a cell, facilitates detection of the cell. Numerous imaging agents are known and described in the literature. By way of example, enzymes, such as β-galactosidase, which are capable of catalyzing a reaction involving a chromogenic substrate may be used. Further by way of example, compounds, the presence of which may be directly detected may be used, such as compounds which emit gamma radiation or which fluoresce, which may be detected using an appropriate detection apparatus An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, "modulating or effecting a process" means stimulating or inhibiting or blocking a process with modulators/effectors thereof, e.g., drugs, compounds, antibodies, biologically active nucleic acids, such as antisense molecules, RNAi molecules, or ribozymes, aptamers, peptides or low-molecular weight organic compounds recognizing said polynucleotides or polypeptides.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" typically refers to short polypeptides.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

A "recombinant polypeptide" is one which is produced upon expression of a recombinant polynucleotide.

A peptide encompasses a sequence of 2 or more amino acids wherein the amino acids are naturally occurring or synthetic (non-naturally occurring) amino acids.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

By the term "specifically binds," as used herein, is meant a molecule which recognizes and binds a specific second molecule, but does not substantially recognize or bind other molecules in a sample, or it means binding between two or more proteins as in part of a cellular regulatory process, where said proteins do not substantially recognize or bind other proteins in a sample.

The term "standard," as used herein, refers to something used for comparison. For example, it can be a known standard agent or compound which is administered or added and used for comparing results when adding a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

The term "stimulate" as used herein, means to induce or increase an activity or function level such that it is higher relative to a control value. The stimulation can be via direct or indirect mechanisms. In one aspect, the activity or differentiation is stimulated by at least 10% compared to a control value, more preferably by at least 25%, and even more preferably by at least 50%. The term "stimulator" as used herein, refers to any compound or agent, the application of which results in the stimulation of a process or function of interest.

A "subject" of diagnosis or treatment is a mammal, including a human.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "treating" includes prophylaxis of the specific disease, disorder, or condition, or alleviation of the symptoms associated with a specific disease, disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

Although any methods and materials similar or equivalent to those described herein can be used in the practice or testing of the present invention, the preferred methods and materials are described herein.

One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

In accordance with the present invention, as described above or as discussed in the Examples below, there can be employed conventional clinical, chemical, cellular, histochemical, biochemical, molecular biology, microbiology, and recombinant DNA techniques which are known to those of ordinary skill in the art. Such techniques are fully explained in the literature.

Methods of Diagnosing and Treating Fibrotic Disease

The present invention relates to methods of diagnosing a subject with a fibrotic or fibroproliferative disease or disorder based on the unexpected findings that circulating fibrocyte levels and CXCL12 levels are significantly elevated in peripheral blood and fibrotic tissue of patients with a fibrotic disease.

The present invention includes methods of diagnosing a test subject with a fibrotic disease or disorder comprising determining the number of circulating fibrocytes in the test subject and comparing to the number of circulating fibrocytes in a control subject who does not have a fibrotic disease. The number of circulating fibrocytes is determined by obtaining a tissue sample from the test subject and comparing the sample to a sample from the control subject. The tissue sample can be a peripheral blood sample. The tissue sample can be obtained from venipuncture or biopsy using methods known in the art. Fibrocyte counts can then be quantitated by methods known in the art for determining cell counts. Fibrocyte counts can be determined directly (e.g., by counting fibrocytes) or indirectly (e.g., by counting an indicator of fibrocytes). In one embodiment, the number of fibrocytes is determined flow cytometry, fluorescence activated cell sorting (FACS), or magnetic activated cell sorting (MACS) [10, 22, 23, 29].

A subject can be determined to have a fibrotic disease or condition if the test subject is found to have a greater number of circulating peripheral blood fibrocytes than the control subject. The test subject can have at least about 5% or greater, at least about 10% or greater, at least about 20% or greater, at least about 30% or greater, at least about 40% or greater, at least about 50% or greater, at least about 60% or greater, at least about 70% or greater, at least about 80% or greater, at least about 90% or greater, or at least about 100% or greater number of circulating fibrocytes than a normal subject. In another embodiment, the number of circulating fibrocytes in a subject with a fibrotic disease or disorder is at least about two fold, at least about three fold, at least about four fold, at least about five fold, at least about six fold, or at least about seven fold greater than greater than in a normal subject. In one embodiment, the number of circulating fibrocytes in a subject with a fibrotic disease or disorder is at least about 10 fold greater than the number of circulating fibrocytes in a normal subject.

The present invention includes methods of diagnosing a test subject with a fibrotic disease or disorder comprising determining the amount of CXCL-12 in the test subject and comparing to the amount of CXCL-12 in a control subject who does not have a fibrotic disease. The amount of CXCL-12 is determined by obtaining a tissue sample from the test subject and comparing the sample to a sample from the control subject. The tissue sample can be a peripheral blood sample. The tissue sample can be obtained from venipuncture or biopsy using methods known in the art. The amount of CXCL-12 can then be quantitated by methods known in the art, for instance, by enzyme-linked immunosorbent assays (ELISAs), radioimmunoassays (RIAs), immunohistochemical staining, and fluorescence activated cell sorting (FACS) [10].

In one embodiment, the amount of circulating CXCL12 in a subject with a fibrotic disease or disorder is at least about 10% greater, at least about 20% greater, at least about 30% greater, at least about 40% greater, at least about 50% greater, at least about 60% greater, at least about 70% greater, at least about 80% greater, at least about 90% greater, at least about 100% greater, or at least about 500% greater than in a normal subject. In another embodiment, the amount of circulating CXCL12 in a subject with a fibrotic disease or disorder is at least about 1000% greater than in a normal subject.

The diagnostic methods of the invention can be used to not only determine whether a test subject has a fibrotic disease, but can also be used to indicate the severity or progression of the fibrotic disease. It is believed that as the severity of the disease increases or fibrosis progresses, the circulating number of fibrocytes as well as amount of CXCL12 also increases. In one embodiment of the invention, the number of circulating fibrocytes and/or amount of CXCL12 can be used to determine the disease status of a test subject with a known fibrotic disease at an unknown stage of severity or progression. In this embodiment, the number of circulating fibrocytes and/or amount of CXCL12a from a test sample of the test subject with a known fibrotic disease is compared to that of a control subject with the same fibrotic disease at a known stage. A statistically same number of circulating fibrocytes and/or statistically same amount of CXCL12 in a test subject as in the control subject is indicative that the test subject has the same stage of fibrotic disease as the control subject.

The invention also includes methods of treating a fibrotic disease or condition in a subject suffering from a fibrotic disease or condition by administering a therapeutic that reduces the number of circulating fibrocytes. The therapeutic can be a drug or biologic (e.g., antibody, anti-sense nucleic acid, RNAi, toxin, peptide, fusion protein, mimetic peptide, aptamer, etc.). In one embodiment of the invention, the therapeutic modifies the trafficking of fibrocytes.

In one embodiment, the therapeutic reduces the number of circulating fibrocytes by at least about 5%, at least about 10%, at least about 20%, at least about 30%, at least about 40%, or at least about 50% or more compared to the number of circulating fibrocytes in the subject prior to treatment. In yet another embodiment, the therapeutic reduces the number of circulating fibrocytes by at least about two fold, at least about 3 fold, at least about 4 fold, or at least about five fold compared to the number of circulating fibrocytes in the subject prior to treatment.

As can be appreciated by a skilled artisan, the therapeutic administered to a subject suffering from a fibrotic disease should be administered at a therapeutically effective dose. The therapeutic may alleviate symptoms and discomfort associated with the fibrotic disease, thereby acting as a prophylactic agent.

In one embodiment, the therapeutic also reduces the levels of circulating CXCL12 in the subject. In one embodiment of the invention, the invention blocks the expression of a chemokine receptor necessary for the trafficking of fibrocytes.

In one embodiment, the therapeutic reduces the amount of CXCL12 by at least about 5%, at least about 10%, at least about 20%, at least about 30%, at least about 40%, or at least about 50% or more compared to the amount of CXCL12 in the subject prior to treatment. In one embodiment of the invention, the CXCL12 is plasma CXCL12.

In yet another embodiment, the therapeutic also reduces the total percentage of circulating fibrocytes expressing α-SMA. In one embodiment, the therapeutic reduces the total percentage of circulating fibrocytes expressing α-SMA by at least about 5%, at least about 10%, at least about 20%, at least about 30%, at least about 40%, or at least about 50% or more compared to the total percentage of circulating fibrocytes expressing α-SMA in the subject prior to treatment.

The treatment methods of the invention can also be used as a preventative measure to reduce the severity or progression of a fibrotic disease or disorder. For instance, therapeutic agents which reduce the total number of circulating fibrocytes can be administered to a patient at risk for developing a fibrotic disease or disorder or at risk for progression of a fibrotic disease or disorder. For instance, therapeutic agents that reduce the total number of circulating fibrocytes can be administered to patients before, during, and after surgery, chemotherapy, or radiation treatment. Such agents can also be administered during or after an acute event associated with fibrosis such as a myocardial infarction or an acute lung injury. Further, the invention includes administration of a drug or biologic to prevent secondary fibrosis that is associated with a primary disease.

Some examples of diseases, disorders, and conditions which may be diagnosed and treated according to the methods of the invention are discussed herein. The invention should not be construed as being limited solely to these examples, as other diseases, disorders and conditions, which are at present unknown, once known, may also be treatable using the methods of the invention.

Fibrotic diseases can occur in virtually every organ and system of the body. The methods of the invention can be used to diagnose, prevent, and treat fibrotic disease in all organs of the body and vasculature, including, for instance, the lungs, heart, kidneys, liver, skin, and gall bladder. Fibrotic diseases and conditions that can be diagnosed, prevented or treated by the methods of the invention include, but are not limited to, idiopathic pulmonary fibrosis, fibrotic interstitial lung disease, interstitial pneumonia, fibrotic variant of non-specific interstitial pneumonia, cystic fibrosis, lung fibrosis, silicosis, asbestosis, asthma, chronic obstructive pulmonary lung disease (COPD), pulmonary arterial hypertension, liver fibrosis, liver cirrhosis, renal fibrosis, glomerulosclerosis, x kidney fibrosis, diabetic nephropathy, heart disease, fibrotic valvular heart disease, systemic fibrosis, rheumatoid arthritis, excessive scarring resulting from surgery, chemotherapeutic drug-induced fibrosis, radiation-induced fibrosis, macular degeneration, retinal and vitreal retinopathy, atherosclerosis, and restenosis.

Further, although the present invention is directed to methods of preventing and treating fibrotic diseases, it is contemplated that the methods could also be extended to preventing and treating diseases and disorders associated with angiogenesis. Proangiogenesis factors are elicited by fibrotic tissue and may lead to the development of a secondary pathology related to angiogenesis such as cancer. Further, cancer-associated fibroblasts are associated with some cancers. Accordingly, the methods of the invention include methods of treating and preventing angiogenesis events secondary to fibrotic disease by administering a drug or biologic capable of reducing the number of circulating fibrocytes.

Antibodies

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals utilizing the technology described in international application no. PCT/US90/02545, which is incorporated by reference herein in its entirety.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12 (3,4):125-168) and the references cited therein. Further, the antibody of the invention may be "humanized" using the technology described in Wright et al., (supra) and in the references cited therein, and in Gu et al. (1997, Thrombosis and Hematocyst 77 (4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

Peptides

The peptides of the present invention may be readily prepared by standard, well-established techniques, such as solid-phase peptide synthesis (SPPS) as described by Stewart et al., in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Nucleic Acids

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO 2-CH2), 2'-O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified.

The term nucleic acid also specifically includes nucleic acids composed of bases other than the five biologically occurring bases (adenine, guanine, thymine, cytosine and uracil).

Pharmaceutical Compositions

The invention also encompasses the use pharmaceutical compositions to practice the methods of the invention, the compositions comprising an appropriate compound, or an analog, derivative, or modification thereof, and a pharmaceutically-acceptable carrier.

As used herein, the term "pharmaceutically-acceptable carrier" means a chemical composition with which an appropriate compound may be combined and which, following the combination, can be used to administer the appropriate compound to a mammal.

The pharmaceutical compositions useful for practicing the invention may be administered to deliver a dose of between 1 ng/kg/day and 100 mg/kg/day. In one embodiment, the invention envisions administration of a dose which results in a concentration of hypericin between 1 $\mu$M and 10 $\mu$M in a compound-sensitive-disease-affected tissue of a mammal during illumination of a dermatological tissue or of a blood tissue of the mammal.

Pharmaceutical compositions that are useful in the methods of the invention may be administered systemically in oral solid formulations, ophthalmic, suppository, aerosol, topical or other similar formulations. Such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate hypericin derivative according to the methods of the invention.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal, venous, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion. As used herein, an "oily" liquid is one which comprises a carbon-containing liquid molecule and which exhibits a less polar character than water.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

Kits

The invention also includes a kit comprising the composition of the invention and an instructional material which describes administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Materials and Methods

Patients and Samples

Patients were recruited from the interstitial lung disease clinic at UCLA and all work was approved by the Institutional Review Board. Lung tissue samples from patients with fibrotic lung disease were obtained during open lung biopsy for the diagnosis of interstitial lung disease, and normal samples were obtained from patients who underwent lobectomy for bronchogenic carcinoma, at a site distant from the malignancy. Samples were homogenized and sonicated in complete buffer (Roche Diagnostics, Indianapolis, Ind., USA) as previously described [14]. Homogenates were centrifuged at 900×g for 15 minutes, filtered through 1.2 μm sterile Acrodiscs (Gelman Sciences, Ann Arbor, Mich., USA). We also obtained 10 ml of heparinized venous blood from 5 normal volunteers and 5 patients with fibrotic interstitial lung disease. Of the patients with fibrotic interstitial lung disease, four were diagnosed with UIP on the basis of clinical, radiographic, and histopathologic features, and one was diagnosed with fibrotic NSIP on the basis of histopathology. Samples were processed to isolate the buffy coat leukocyte populations for FACS analysis by centrifugation, as previously described [15, 16]. Contaminating red blood cells were removed then the cells were washed and brought up to a concentration of $1 \times 10^7$/ml in PBS containing 0.1% FBS. Lung homogenates and plasma samples were frozen at −70° C. until processed for ELISA. Samples were assayed for CXCL12 levels as previously described [17].

Immunohistochemical Staining

Paraffin embedded tissues were processed for immunohistochemical localization of CXCL12 as previously described [18]. Briefly, tissue sections were dewaxed with xylene and rehydrated through graded concentrations of ethanol. The slides were fixed for 30 minutes in 1:1 absolute methanol and 3% $H_2O_2$, rinsed in PBS and then nonspecific binding sites were blocked with universal blocking reagent (Biogenex, San Ramon, Calif.) by incubation at room temperature for 30 min. Following the blocking step, a 1:500 dilution of either control (goat) or goat anti-hCXCL12 serum was added as a primary antibody, and slides were incubated for 30 minutes at room temperature. Slides were then rinsed with PBS, overlaid with biotinylated anti-goat IgG (Vector ABC Elite Kit, Vector Laboratories, Burlingame, Calif.) and incubated for an additional 30 min. Slides were rinsed 2 times with PBS, and were then treated with streptavidin-conjugated peroxidase for 30 min at room temperature. Following, three washes with PBS, the slides were subjected to colorimetric detection using the substrate chromogen 3,3'-diaminobenzidine (DAB, Vector Laboratories). Slides were incubated for 5-10 min in DAB solution at room temperature to allow color development, and rinsed with distilled water to quench the reaction. Mayer's hematoxylin was used as a counterstain.

Flow Cytometry

Circulating fibrocytes were identified by flow cytometry according to previously published methods [17]. Briefly, leukocytes were stained with anti-CXCR4-FITC (R&D systems), and anti-CD45-PerCP (BD Biosciences). Next, the cells were permeabilized using cytofix/cytoperm (BD Biosciences) prior to intracellular staining of collagen-I (Col I, Rockland) and αSMA (R&D Systems). Col-I and αSMA were then stained with unconjugated rabbit anti-human Col-I and mouse anti-human αSMA Abs followed by Alexa Fluor 610-R-phycoerythrin goat anti-rabbit or mouse (Molecular Probes). Samples were processed on a FACS Calibur flow cytometer using Cellquest software.

Statistical Analysis

Data were analyzed on a Dell PC (Dell, Round Rock, Tex., USA) computer using Statview statistical package (Abacus Concepts, Berkeley, Calif., USA). Comparisons were evaluated by Student's unpaired t test. Results were considered statistically significant if p values were less than 0.05.

Results

Figure 1B:
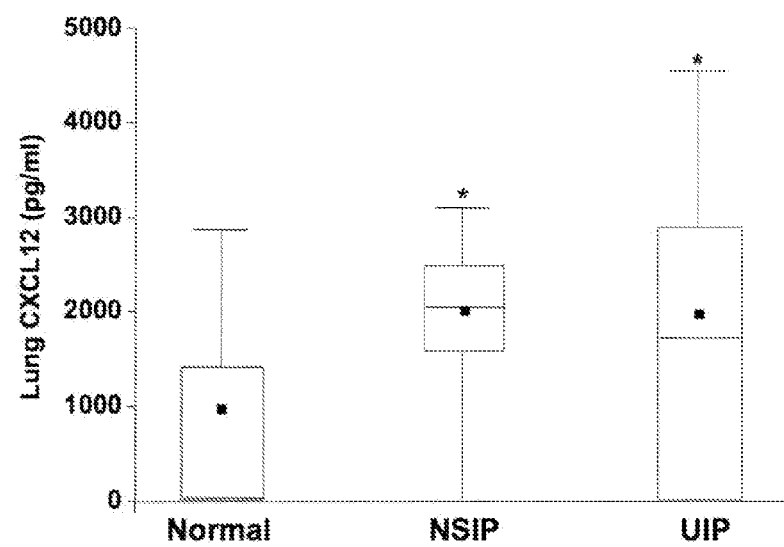

Given the role of the chemokine ligand, CXCL12, in recruiting fibrocytes to the lung in animal models of pulmonary fibrosis, we began by comparing the lung expression of CXCL12 in biopsy tissue in archived samples obtained from patients with fibrotic lung disease. We found extensive accumulation of CXCL12 in lung tissue from patients with the clinical and histologic diagnosis UIP, as detected by immunohistochemistry (FIG. 1a). To assess this finding quantitatively, we compared protein levels of CXCL12 in lung tissue from patients with UIP and fibrotic NSIP, and compared them to levels in normal lung tissue (FIG. 1b). We noted a 64% and 77% increase in lung CXCL12 levels in lungs of patients with fibrotic NSIP and UIP, respectively, as compared to normal lungs. Interestingly, the levels of CXCL12 did not differ between NSIP and UIP.

Figure 2:
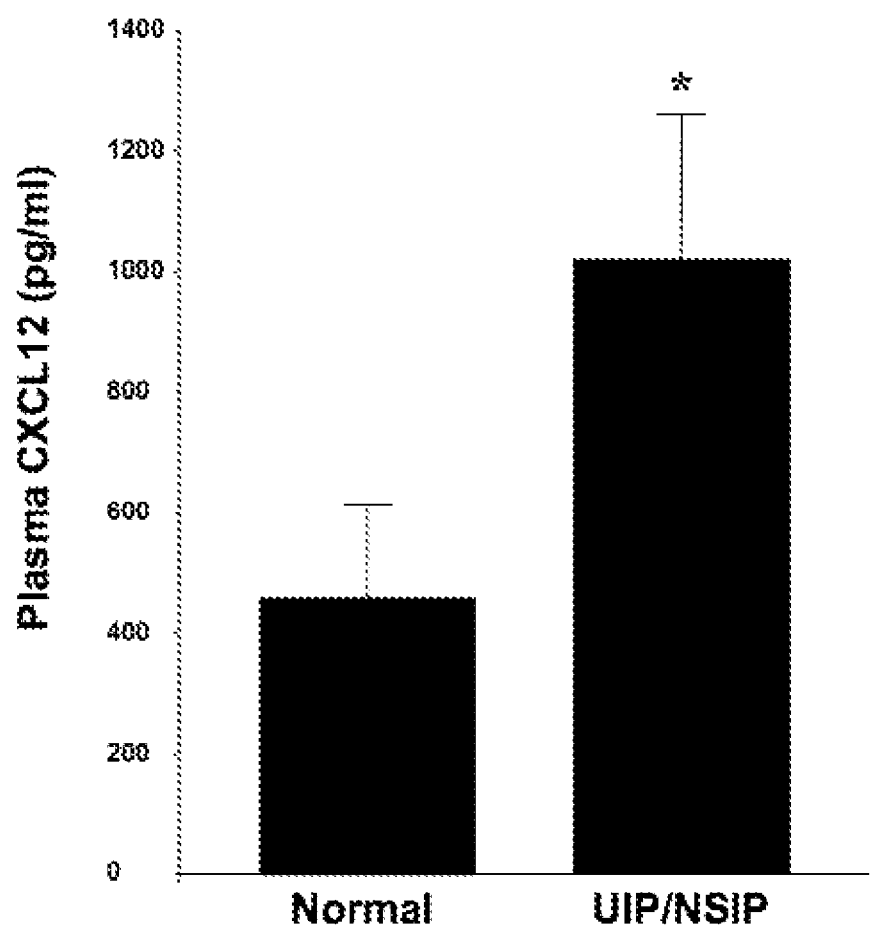
FIG. 2. Plasma CXCL12 level in fibrotic interstitial lung disease. Data represent mean±SEM of n of 5 patients per group. "UIP/NSIP," patients with UIP or fibrotic NSIP; *, p<0.05 compared to samples from normal volunteers.

In order to examine whether this increased expression of lung CXCL12 in patients with fibrotic lung disease was correlated with fibrocyte trafficking, we next performed a pilot study, in which we prospectively collected peripheral blood from five patients with UIP or fibrotic NSIP and compared them to five normal volunteers. We began by comparing the plasma CXCL12 levels between the groups, since plasma chemokine levels have previously been shown to correlate with tissue levels in pulmonary fibrosis [19]. The plasma CXCL12 levels were 2.4-fold higher in patients with UIP and fibrotic NSIP than normal patients (FIG. 2), confirming our observation in lung tissues.

Figure 3A:
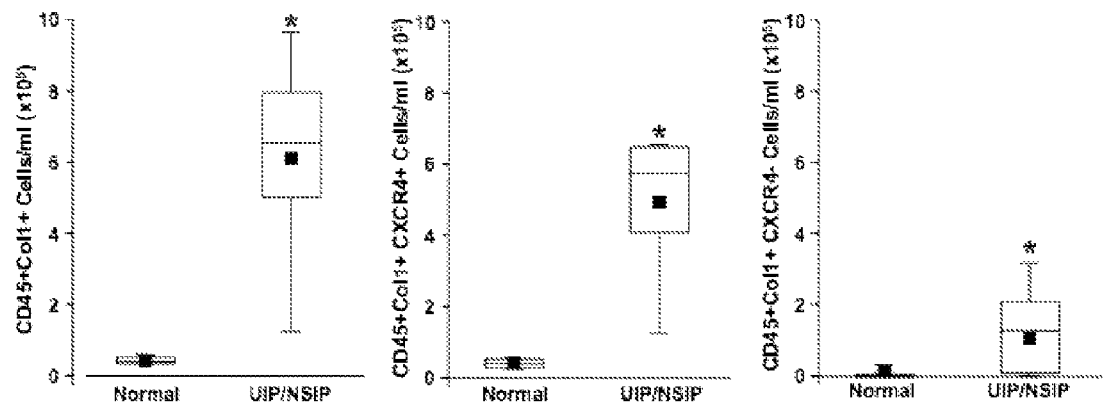
FIG. 3. Circulating fibrocytes in fibrotic interstitial lung disease. Panels (a) and (b) represent numbers of circulating $CD45^+$ collagen-$I^+$ cells and $CD45^+$ collagen-$I^+$ $\alpha SMA^+$ cells, respectively. Box and whiskers represent 25th-75th and 10th-90th percentiles, respectively; small squares and transverse lines represent the mean and median, respectively. "UIP/NSIP," patients with UIP or fibrotic NSIP; *, p<0.05 compared to normal volunteers (n=5 patients per group).

Next we compared the number of circulating fibrocytes in the two groups by enumerating collagen-I expressing CD45[+] cells [17]. Remarkably, patients with fibrotic lung disease had an order of magnitude higher number of circulating fibrocytes as compared to healthy volunteers (FIG. 3a). We have previously reported that circulating fibrocytes are composed of a larger CXCR4-positive and a smaller CXCR4-negative subsets [13]. The expanded circulating fibrocyte pool was most notable in the CXCR4-expressing subset, but was also noted in the CXCR4-negative subset (FIG. 3a).

Figure 3B:
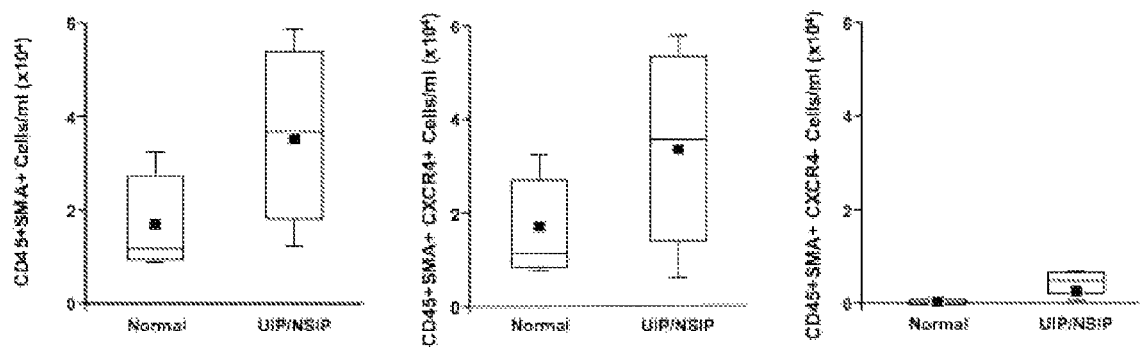

Many of the lung fibroblasts in pulmonary fibrosis have myofibroblast phenotype and the contractile properties of myofibroblasts have been hypothesized to be important in the progression of lung fibrosis [6, 20, 21]. Since circulating fibrocytes are capable of differentiating into myofibroblasts both in culture and in vivo [22, 23], we also compared the degree of differentiation of the circulating fibrocytes in the two groups by assessing them for the expression of the myofibroblast marker, α-SMA (FIG. 3b). The αSMA-expressing fibrocytes constituted a small subset of total circulating fibrocytes in both groups. Although we observed no statistically significant difference between total αSMA$^+$ fibrocytes or the CXCR4$^+$ or CXCR4$^-$ subsets of αSMA$^+$ fibrocytes between patients and normal volunteers, there appeared to be a trend toward higher numbers of circulating of αSMA$^+$ cells in patients with fibrotic interstitial lung diseases. This suggests that the greater numbers of circulating fibrocytes in patients with fibrotic interstitial lung diseases may, in addition, show early evidence of differentiation to myofibroblast phenotype.

Discussion

Fibrocytes are a recently identified population of bone marrow-derived circulating cells that express markers for both hematopoietic cells and fibroblasts. Prior evidence has linked circulating fibrocytes to the biology of wound repair, scleroderma, and asthma, via their differentiation into fibroblasts and myofibroblasts (reviewed in refs. [11, 12]). Fibrocytes are, in addition, capable of differentiating into diverse cell types, including adipocytes and antigen-presenting cells [13, 24].

We recently identified fibrocytes as contributing to lung scarring in the mouse model of bleomycin-induced pulmonary fibrosis and demonstrated that both mouse and human fibrocytes can traffic to the lung via the CXCL12-CXCR4 axis in the context of this model [10]. While intrapulmonary administration of pro-fibrotic agents represent the dominant animal models for the study of fibrotic lung diseases, they differ from the human disease in several key respects, including temporal progression and histology [25, 26]. This prompted us to examine the relevance of fibrocytes in patients with fibrotic interstitial lung diseases in the current study. We found increased expression of the fibrocyte-attracting chemokine, CXCL12, in the lungs and plasma of patients with fibrotic interstitial lung disease. In addition, we found as well as a marked expansion of circulating fibrocyte pool in these patients: fibrocytes, which normally constitute ~0.5% of circulating leukocytes [11, 12], comprised 6-10% of leukocytes in our cohort. Indeed, these cells may have contributed to a peripheral blood monocytosis observed in this cohort (absolute monocyte count $4.54 \pm 0.44 \times 10^9$ cells/L in this cohort; reference range $0.10-1.10 \times 10^9$ cells/L, $p=0.004$). To our knowledge, this is the first reported evidence of the involvement of fibrocytes in human interstitial lung disease.

The current report has a number of implications for future work. First, the mechanism of fibrocyte function in the pathogenesis of pulmonary fibrosis is now of great interest. In addition to fibrocyte generation of extracellular matrix and contractile properties as fibroblasts/myofibroblasts, fibrocytes may conceivably play a role in angiogenesis or on-going immune responses in these illnesses [24, 27]. Second, the relative contribution of fibrocytes, local precursor cells, and pre-existing lung fibroblasts to the final lung pathology of human pulmonary fibrosis is yet to be established. Third, the role of CXCR4$^+$ and CXCR4$^-$ fibrocyte subsets in the progression of these diseases should be determined. Finally, the study of mechanisms of fibrocyte traffic, including their egress from bone marrow, endothelial adhesion and egress from the circulation, and response to chemokine gradients, may represent novel targets for therapeutic intervention in these devastating disorders.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

BIBLIOGRAPHY

The references as cited throughout this document and below are hereby incorporated by reference herein in their entirety.

[1] anonymous, American Thoracic Society. Idiopathic pulmonary fibrosis: diagnosis and treatment. International consensus statement. American Thoracic Society (ATS), and the European Respiratory Society (ERS), American Journal of Respiratory & Critical Care Medicine 161 (2000) 646-664.

[2] S. American Thoracic, and S. European Respiratory, American Thoracic Society/European Respiratory Society International Multidisciplinary Consensus Classification of the Idiopathic Interstitial Pneumonias., American Journal of Respiratory & Critical Care Medicine 165 (2002) 277-304.

[3] S. Nagai et al. Clin Chest Med 25 (2004) 705-715, vi.

[4] A. L. Katzenstein, and J. L. Myers, Am J Respir Crit Care Med 157 (1998) 1301-1315.

[5] W. D. Travis et al., Am J Surg Pathol 24 (2000) 19-33.

[6] C. Kuhn, and J. A. McDonald, Am J Pathol 138 (1991) 1257-1265.

[7] A. G. Nicholson et al., Am J Respir Crit Care Med 166 (2002) 173-177.

[8] T. E. King, Jr. et al., Am J Respir Crit Care Med 164 (2001) 1025-1032.

[9] K. K. Kim et al., Proc Natl Acad Sci USA 103 (2006) 13180-13185.

[10] R. J. Phillips et al., Journal of Clinical Investigation 114 (2004) 438-446.

[11] C. N. Metz, Cell Mol Life Sci 60 (2003) 1342-1350.

[12] T. E. Quan et al., Int J Biochem Cell Biol 36 (2004) 598-606.

[13] K. M. Hong et al., FASEB Journal 19 (2005) 2029-2031.

[14] M. P. Keane et al., J Immunol 163 (1999) 5686-5692.

[15] J. M. Ham et al., Chemotactic cytokine (IL-8 and MCP-1) gene expression by human whole blood, Immunol Invest 20 (1991) 387-394.

[16] R. M. Strieter et al., J Leukoc Biol 47 (1990) 366-370.

[17] R. J. Phillips et al., J Clin Invest 114 (2004) 438-446.

[18] D. A. Arenberg et al., J Clin Invest 97 (1996) 2792-2802.
[19] R. M. Strieter et al., Am J Respir Crit Care Med 170 (2004) 133-140.
[20] S. H. Phan, The myofibroblast in pulmonary fibrosis, Chest 122 (2002) 286S-289S.
[21] Z. Xing et al., Am J Pathol 150 (1997) 59-66.
[22] R. Abe et al., J Immunol 166 (2001) 7556-7562.
[23] M. Schmidt et al., J Immunol 171 (2003) 380-389.
[24] J. Chesney et al., Proc Natl Acad Sci USA 94 (1997) 6307-6312.
[25] P. W. Noble, Clin Chest Med 27 (2006) S11-16, v.
[26] M. Gharaee-Kermani et al., Methods Mol Med 117 (2005) 251-259.
[27] I. Hartlapp et al., Faseb J 15 (2001) 2215-2224.
[28] Wynn, Nature Rev. Immunol. (2004) 4, 583.
[29] Bucala, et al., Mol. Med. 1 (1994) 71-81

We claim:

1. A method of diagnosing a human subject with a fibrotic lung disease comprising determining the amount of circulating CXCL-12 in said subject, wherein an increase in the amount of circulating CXCL-12 in said subject compared to the amount of circulating CXCL-12 in a control subject is indicative of a fibrotic lung disease.

2. The method of claim 1, wherein said fibrotic lung disease is selected from the group consisting of idiopathic pulmonary fibrosis, fibrotic interstitial lung disease, interstitial pneumonia, fibrotic variant of non-specific interstitial pneumonia, cystic fibrosis, lung fibrosis, chronic obstructive pulmonary lung disease (COPD), and pulmonary arterial hypertension.

3. The method of claim 1, wherein said fibrotic lung disease is interstitial pneumonia or non-specific interstitial pneumonia.

4. The method of claim 1, wherein the amount of circulating CXCL-12 in said subject is at least about 10% greater, at least about 20% greater, at least about 30% greater, or at least about 50% greater than the amount of circulating CXCL-12 in said control subject.

5. The method of claim 1, wherein said amount of circulating CXCL-12 in said subject is least about 2 times greater, or at least about 5 times greater than the amount of circulating CXCL-12 in said control subject.

6. The method of claim 1, wherein said circulating CXCL-12 is plasma CXCL-12.

7. The method of claim 1, wherein said control subject is a subject that does not have a fibrotic lung disease.

* * * * *

UNITED STATES PATENT AND TRADEMARK OFFICE
CERTIFICATE OF CORRECTION

PATENT NO. : 8,216,796 B2  
APPLICATION NO. : 13/327025  
DATED : July 10, 2012  
INVENTOR(S) : Borna Mehrad et al.

Page 1 of 1

It is certified that error appears in the above-identified patent and that said Letters Patent is hereby corrected as shown below:

In the Specification

Column 1, line 19, delete "AR055075,".

Signed and Sealed this
Third Day of February, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,216,796 B2 | Page 1 of 1 |
| APPLICATION NO. | : 13/327025 | |
| DATED | : July 10, 2012 | |
| INVENTOR(S) | : Mehrad et al. | |

It is certified that error appears in the above-identified patent and that said Letters Patent is hereby corrected as shown below:

In The Specification

In column 1, line 18-21, delete "supported in part from Grant Nos. HL73848, HL080206, AR055075, CA87879, and HL66027 awarded by the National Institutes of Health. The United States Government" and insert --made with government support under HL066027, HL073848, HL080206, CA087879 awarded by the National Institutes of Health. The government--, therefor Signed and Sealed this
Twenty-sixth Day of April, 2016

Michelle K. Lee
*Director of the United States Patent and Trademark Office*